(12) United States Patent
Broad et al.

(10) Patent No.: US 12,296,193 B2
(45) Date of Patent: May 13, 2025

(54) DEVICES AND METHODS FOR CALIBRATING AND CONTROLLING COLLIMATOR LEAVES

(71) Applicant: Elekta Limited, Crawley (GB)

(72) Inventors: Martin Broad, Crawley (GB); Ralf Spriestersbach, Crawley (GB); Christopher Knox, Crawley (GB)

(73) Assignee: Elekta Limited, Crawley (GB)

( * ) Notice: Subject to any disclaimer, the term of this patent is extended or adjusted under 35 U.S.C. 154(b) by 124 days.

(21) Appl. No.: 17/759,585

(22) PCT Filed: Jan. 29, 2021

(86) PCT No.: PCT/EP2021/052084
§ 371 (c)(1),
(2) Date: Jul. 27, 2022

(87) PCT Pub. No.: WO2021/152076
PCT Pub. Date: Aug. 5, 2021

(65) Prior Publication Data
US 2023/0087238 A1    Mar. 23, 2023

(30) Foreign Application Priority Data
Jan. 31, 2020  (GB) ...................................... 2001391

(51) Int. Cl.
*A61N 5/10*  (2006.01)
(52) U.S. Cl.
CPC .......... *A61N 5/1045* (2013.01); *A61N 5/1075* (2013.01)
(58) Field of Classification Search
None
See application file for complete search history.

(56) References Cited

U.S. PATENT DOCUMENTS

| 10,518,110 B1* | 12/2019 | Jimenez-Carvajal ......... A61N 5/1075 |
| 10,758,748 B2* | 9/2020 | Chappelow .......... A61N 5/1045 |

(Continued)

FOREIGN PATENT DOCUMENTS

| CA | 2522097 C * | 9/2012 | .............. B25J 13/08 |
| CN | 110075428 A | 8/2019 | |

(Continued)

OTHER PUBLICATIONS

"International Application Serial No. PCT/EP2021/052084, International Search Report dated May 7, 2021", (May 7, 2021), 3 pgs.

(Continued)

*Primary Examiner* — Marcus H Taningco
*Assistant Examiner* — Djura Malevic
(74) *Attorney, Agent, or Firm* — Schwegman Lundberg & Woessner, P.A.

(57) ABSTRACT

A computer-implemented method for calibrating a multi-leaf collimator of a radiotherapy device. The multi-leaf collimator comprises a plurality of leaves, each leaf comprising an imaging marker, wherein the radiotherapy device includes an imaging device configured to image the leaves. The method comprises: receiving, from the imaging device, an image of the multi-leaf collimator in a calibration position, wherein in the calibration position the tips of the leaves abut an edge of a rigid calibration block, the edge having a known calibration profile; calculating for each leaf, from the calibration profile and the location of the marker in the image, a minor offset of the marker relative to a reference point; and outputting calibration values based on the calculated minor offsets, wherein at least one leaf of the multi-leaf collimator is controlled based on the calibration values.

20 Claims, 10 Drawing Sheets

(56) References Cited

U.S. PATENT DOCUMENTS

| | | | |
|---|---|---|---|
| 10,888,713 B2* | 1/2021 | Rieger | G21K 1/04 |
| 11,065,472 B2* | 7/2021 | Ma | A61N 5/1048 |
| 11,173,326 B2* | 11/2021 | Yang | A61N 5/1049 |
| 11,491,347 B2* | 11/2022 | Ma | A61N 5/1045 |
| 11,568,494 B1* | 1/2023 | Davis | G06T 7/62 |
| 11,730,977 B2* | 8/2023 | Stahl | A61N 5/1036 |
| | | | 600/1 |
| 11,738,209 B2* | 8/2023 | Ma | G21K 1/046 |
| | | | 378/151 |
| 2006/0072849 A1* | 4/2006 | Marc | A61N 5/1042 |
| | | | 382/128 |
| 2008/0298553 A1* | 12/2008 | Takahashi | G21K 1/046 |
| | | | 378/152 |
| 2009/0010395 A1* | 1/2009 | Ein-Gal | G21K 1/04 |
| | | | 378/150 |
| 2012/0215049 A1* | 8/2012 | Otani | G21K 1/046 |
| | | | 600/1 |
| 2013/0258105 A1* | 10/2013 | Jozsef | G01J 1/4257 |
| | | | 348/143 |
| 2015/0094514 A1* | 4/2015 | Gaudio | A61N 5/1075 |
| | | | 600/1 |
| 2018/0193671 A1* | 7/2018 | Chappelow | A61N 5/1045 |

FOREIGN PATENT DOCUMENTS

| | | |
|---|---|---|
| EP | 2085117 A1 | 8/2009 |
| WO | WO-2016200463 A1 | 12/2016 |

OTHER PUBLICATIONS

"International Application Serial No. PCT/EP2021/052084, Written Opinion dated May 7, 2021", (May 7, 2021), 6 pgs.

"United Kingdom Application Serial No. 2001391.8, Examination Report dated Jul. 23, 2020", (Jul. 23, 2020), 6 pgs.

"Chinese Application No. 202180012214.9, Office Action dated Nov. 5, 2024", w English Translation, (Nov. 5, 2024), 11 pgs.

* cited by examiner

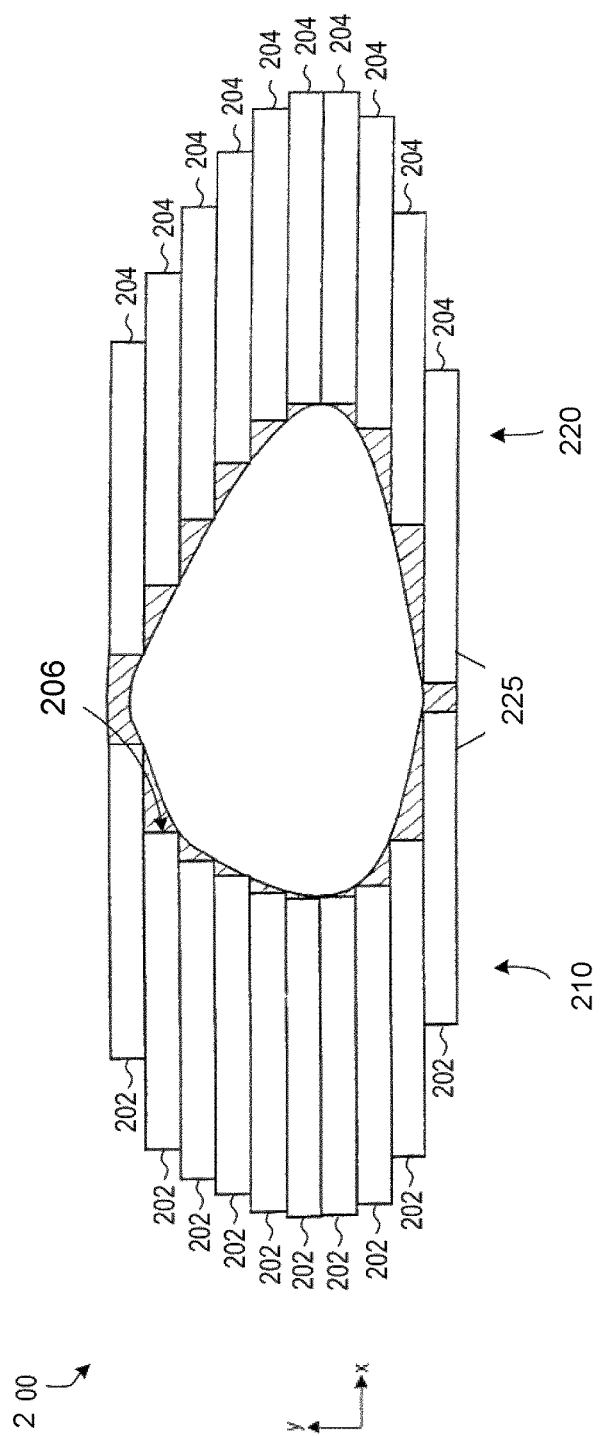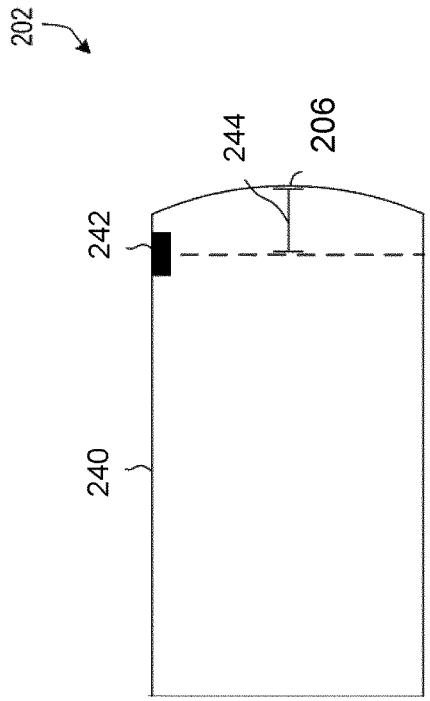
Fig. 2A
Fig. 2B

ND METHODS FOR
DEVICES AND METHODS FOR
CALIBRATING AND CONTROLLING
COLLIMATOR LEAVES

PRIORITY APPLICATIONS

This application is a U.S. National Stage Filing under 35 U.S.C. § 371 from International Application No. PCT/EP2021/052084, filed on Jan. 29, 2021, and published as WO2021/152076 on Aug. 5, 2021, which claims the benefit of priority to United Kingdom Application No. 2001391.8, filed on Jan. 31, 2020; the benefit of priority of each of which is hereby claimed herein, and which applications and publication are hereby incorporated herein by reference in their entireties.

FIELD

This disclosure relates generally to multi-leaf collimators of radiotherapy devices. More specifically, this disclosure relates to devices and methods for calibrating and controlling movement of leaves of a multi-leaf collimator.

BACKGROUND

Radiotherapeutic apparatus involves the production of a beam of ionising radiation, usually x-rays or a beam of electrons or other sub-atomic particles. This is directed towards a cancerous region of a patient, and adversely affects the tumour cells causing an alleviation of the patient's symptoms. The beam is delimited so that the radiation dose is maximised in the tumour cells and minimised in healthy cells of the patient, as this improves the efficiency of treatment and reduces the side effects suffered by a patient.

In a radiotherapy apparatus, the beam can be delimited using a beam limiting device such as a 'multi-leaf collimator' (MLC). This is a collimator which consists of a large number of elongate thin leaves arranged side to side in an array. The leaves are usually made from a high atomic numbered material, usually tungsten, so that they are substantially opaque to the radiation.

Each leaf is moveable longitudinally so that its tip, or leading edge, can be extended into or withdrawn from the radiation beam. All the leaves can be withdrawn to allow the radiation beam to pass through, or all the leaves can be extended so as to block the radiation beam completely. Alternatively, some leaves can be withdrawn and some extended so as to define any desired shape, within operational limits. The array of leaf tips can thus be positioned so as to define a variable edge to the collimator. A multi-leaf collimator usually consists of two banks of such arrays (i.e. leaf banks), each leaf bank projecting into the radiation beam from opposite sides of the collimator. The variable edges provided by the two leaf banks thus collimate the radiation beam to a chosen cross-sectional shape, usually that of a target tumour volume to be irradiated. That is, the two leaf banks combine to provide an aperture of variable shape for shaping the radiation beam.

It is important to accurately control the beam shape, and therefore techniques have been developed to calibrate the positions of collimator leaves.

SUMMARY

Aspects and features of the present invention are described in the accompanying claims.

Disclosed herein are devices and methods for accurately measuring the minor offsets of the collimator leaves. Particular examples of the disclosure enable accurate determination of the positions of the collimator leaves, thus providing more exact positioning of leaves to shape radiation beams during radiotherapy.

BRIEF DESCRIPTION OF THE DRAWINGS

Specific embodiments are described below by way of example only and with reference to the accompanying drawings in which:

FIG. 2A illustrates a top plan view of a leaf array of a multi-leaf collimator;

FIG. 2B is a side view of a leaf of a multi-leaf collimator;

SPECIFIC DESCRIPTION OF CERTAIN EXAMPLE EMBODIMENTS

Given the importance of accurately controlling the beam shape of a radiotherapy device, techniques have been developed to calibrate the positions of collimator leaves.

For example, some radiation-based calibration techniques utilize x-ray film or point dosimeters to confirm that the leaves form the desired radiation beam shape. However, such techniques can be time-consuming and often provide a poor indication of the actual beam geometry. Other calibration techniques involve using a laser beam and optical detector to determine when the MLC leaves have reached a defined calibration position. However, this technique may not provide an accurate indication of the leaf positions for all leaf shape configurations. Still further calibration techniques involve imaging optical markers on the leaves with a camera and using the detected positions of the optical markers to determine the positions of the leaves. However, the lens of the camera can distort the images of the markers, meaning additional calibration steps may be necessary to provide accurate determination of the leaf positions.

In addition, because the optical markers are manually placed on the collimator leaves, the distance between the marker and the leaf tip (a distance known as the "minor offset") is different for each leaf. Existing MLCs cannot simply measure the minor offset with the camera because the leaves are not visible to the camera. For these reasons, existing collimator devices may require computationallyintensive and time-consuming calibration steps to ensure that collimator leaves are correctly positioned during radiotherapy.

The present disclosure provides devices and methods for generating accurate measurements of the minor offsets, such that the true positions of the leaves can be determined without adding excessive calibration time to the machine setup process. As a result, the leaves can be even more accurately placed during radiotherapy so that the desired beam geometry can be achieved. In known systems many tightly tolerance parts are required to achieve a satisfactory calibration accuracy. Due to the high precision and tight tolerances, production costs for many of the components is significantly increased.

It is desirable to provide a method of calibrating a multi-leaf collimator which addresses the abovementioned problems.

Figure 1:
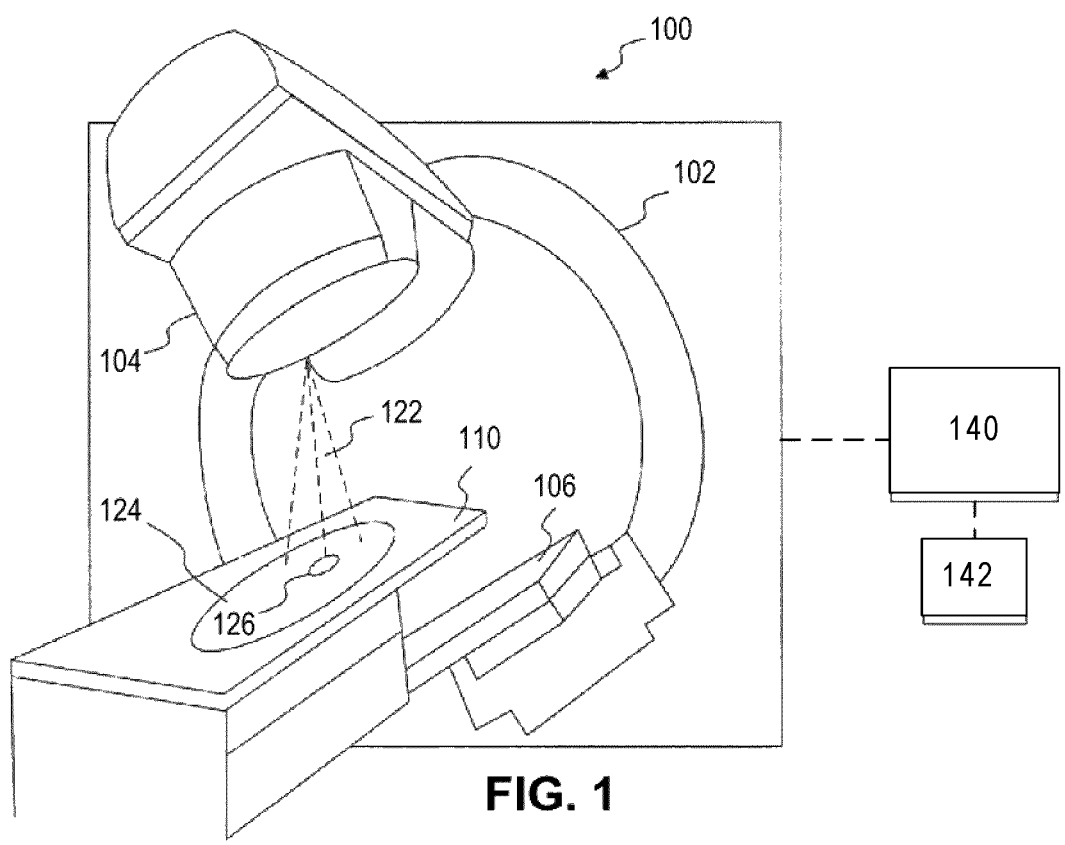
FIG. 1 illustrates a radiotherapy device.

FIG. 1 is a view of an exemplary radiotherapy device 100. Radiotherapy device 100 is, for example, a linear accelerator (LINAC) or a combination magnetic resonance imaging (MRI) and linear accelerator.

Radiotherapy device 100 includes a gantry 102, which supports a radiation head 104 and a detection panel 106. Radiation head 104 and detection panel 106 are mounted opposite each other on gantry 102, with a rotational axis of gantry 102 positioned between them. Radiation head 104 is configured to generate a radiation beam 122 according to a treatment plan to deliver doses of radiation to a patient 124 supported by a couch 110. The gantry 102 is configured to rotate the radiation head 104 and detection panel 106 about the couch 110, to provide patient 124 with a plurality of varying dosages of radiation according to the treatment plan.

Radiation head 104 includes a collimator for collimating the radiation beam 122. The collimator, described below in relation to the other Figures, is a multi-leaf collimator. The radiation head 104 also includes an imaging device for imaging the location of the leaves of the multi-leaf collimator.

In some embodiments, device 100 includes an imaging device, for example is configured as an MR-LINAC device. Exemplary device 100 utilize MR images, CT images, and/or pseudo-CT images to monitor and control radiation delivered by radiation head 104.

The radiotherapy device 100 includes a controller 140 which is programmed to control the radiation head 104, detection panel 106, couch 110, an imaging device, and the gantry. Controller 140 may perform functions or operations such as treatment planning, treatment execution, image acquisition, image processing, motion tracking, motion management, and/or other tasks involved in a radiotherapy process. Hardware components of controller 140 may include one or more computers (e.g., general purpose computers, workstations, servers, terminals, portable/mobile devices, etc.); processors (e.g., central processing units (CPUs), graphics processing units (CPUs), microprocessors, digital signal processors (DSPs), field programmable gate arrays (FPGAs), special-purpose or specially-designed processors, etc.); memory/storage devices such as a memory 142 (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

Controller 140 is programmed to control features of device 100 according to a radiotherapy treatment plan for irradiating a target tissue of a patient. The treatment plan includes information about a particular dose to be applied to a target tissue, as well as other parameters such as beam angles, dose-histogram-volume information, the number of radiation beams to be used during therapy, the dose per beam, and the like. Controller 140 is programmed to control various components of device 100, such as gantry 102, radiation head 104, detection panel 106, and couch 110, according to the predetermined treatment plan.

FIG. 2A is a top plan view of an exemplary leaf array of MLC 200, and FIG. 2B is a side view of an exemplary leaf 202.

MLC 200 includes a plurality of elongate leaves 202, 204 oriented orthogonal to the axis of beam 122, which in the top plan view of the MLC 200 in FIG. 2A is travelling in a direction into the page. During radiotherapy treatment, the leaves of MLC 200 are controlled to take different positions to selectively block some or all of radiation beam 122, thereby altering the shape of the beam that reaches the patient.

MLC 200 includes two banks 210, 220 of leaves, each leaf of which can be individually extended into and out of the path of radiation beam 122 so that their respective tips 206 shape the cross-section of the beam by blocking portions thereof. The word "tip" may refer to a functional end of leaf 202 along a longitudinal axis thereof for purposes of forming a shaping window for radiation beam 122. The word "tip" does not necessarily refer to the end point of leaf 202 relative to the longitudinal axis thereof (that is, the point of the leaf 202 closest to the centre of MLC 200), although in some embodiments it may refer to the end point of leaf 202 relative to the longitudinal axis thereof. In some embodiments, MLC 200 includes a bank of motors, each configured to move a corresponding one of the leaves. Movement of each leaf by the motors is controlled by controller 140. For example, controller 140 controls placement of the leaf tips 206 via the motors to shape radiation beam 122 for irradiating a target tissue 300, such as according to a predetermined treatment plan. In some embodiments, leaves 202, 204 are configured to be extended into the path of radiation beam 122 to a location beyond a halfway point between leaf banks 210, 220, allowing the leaves 202, 204 to be fully closed together.

Radiation head 104 also includes an imaging device, such as a camera, configured to view collimator leaves 202, 204. Leaves 202, 204 may not be visible to camera; accordingly, leaves 202, 204 include imaging markers mounted thereon, such as rubies or fluorescing markers, which are visible to the camera.

According to embodiments in which leaves 202, 204 each include a ruby as an imaging marker, the ruby is configured to fluoresce in the dark red/near infrared light band (e.g. 695 nm) when illuminated with light having a wavelength in the 525 nm green light band or in the 410 nm violet/near ultraviolet light band. The camera generates image data of the leaves 202, 204 utilizing the light emitted by the rubies. The controller 140 utilizes the image data to determine the position of the leaves and to control movement of the leaves into or out of the path of radiation beam 122 so as to shape the beam (e.g. according to a predetermined treatment plan).

Leaves 202, 204 are constructed of a radiopaque material such as tungsten and arranged side-by-side relative to each other, in two opposing banks 210, 220; thus, areas beneath the leaves 202, 204 are not irradiated. Each leaf is positioned directly opposite a corresponding leaf in the other leaf bank;

two opposing leaves constitute a leaf pair 225. Each leaf is thin in its transverse (y) direction to provide high resolution and limit the size of unnecessarily irradiated tissue areas. Each leaf is also deep in the (z) direction to provide effective radiation absorption.

The MLC has a centreline half way between the banks of opposing leaves. That is, the centreline is equidistant between the first bank of leaves 210 and the second bank of leaves 220. The camera is centred on the centreline of the MLC. For example, the MLC has four reference markers, such as rubies, mounted above the MLC and symmetrically positioned about the centreline. An optical mechanical workflow and adjustment aligns the camera and lens (centre of image) with these rubies. The block is fixed in the mechanical/beam centre of the MLC, since all the calibration and distortion calculations are calculated from the centre of the image/centre of the camera lens which coincides with beam centre. Therefore, images of the MLC from the camera are centred on the centreline.

As is visible from FIG. 2B, which shows a side view of an exemplary leaf 202, the leaf includes a body 240 constructed of a radiopaque material such as tungsten. The leaf 202 also includes an imaging marker 242 (e.g. a ruby) positioned near the leaf tip 206. The imaging marker 242 of each leaf is manually placed approximately a predetermined distance from leaf tip 206. For example, imaging marker 242 may be placed such that its centre is approximately 4.5 millimetres from leaf tip 206. However, because each imaging marker is manually placed, the minor offset 244 between the centre of imaging marker 242 and the leaf tip 206 may be different for each leaf. The camera cannot measure minor offset 244 by imaging the position of the leaf tip 206 because leaf 202 is not visible to the camera except for imaging marker 242. Therefore a technique is required to determine the minor offset, i.e. the precise distance from the centre of the imaging marker 242 to the leaf tip 206, so that the precise location of the leaf tip 206 can be accurately determined from an image from the camera which shows the marker 242.

The leaves of MLC 200 may be identically shaped and dimensioned; for example, the leaf length, length of drive coupling, and length of body may be constant for all leaves of MLC 200. However, because each marker 242 is manually and individually placed, minor offset 244 may vary across the leaves.

Calibrating the MLC

Figure 3:
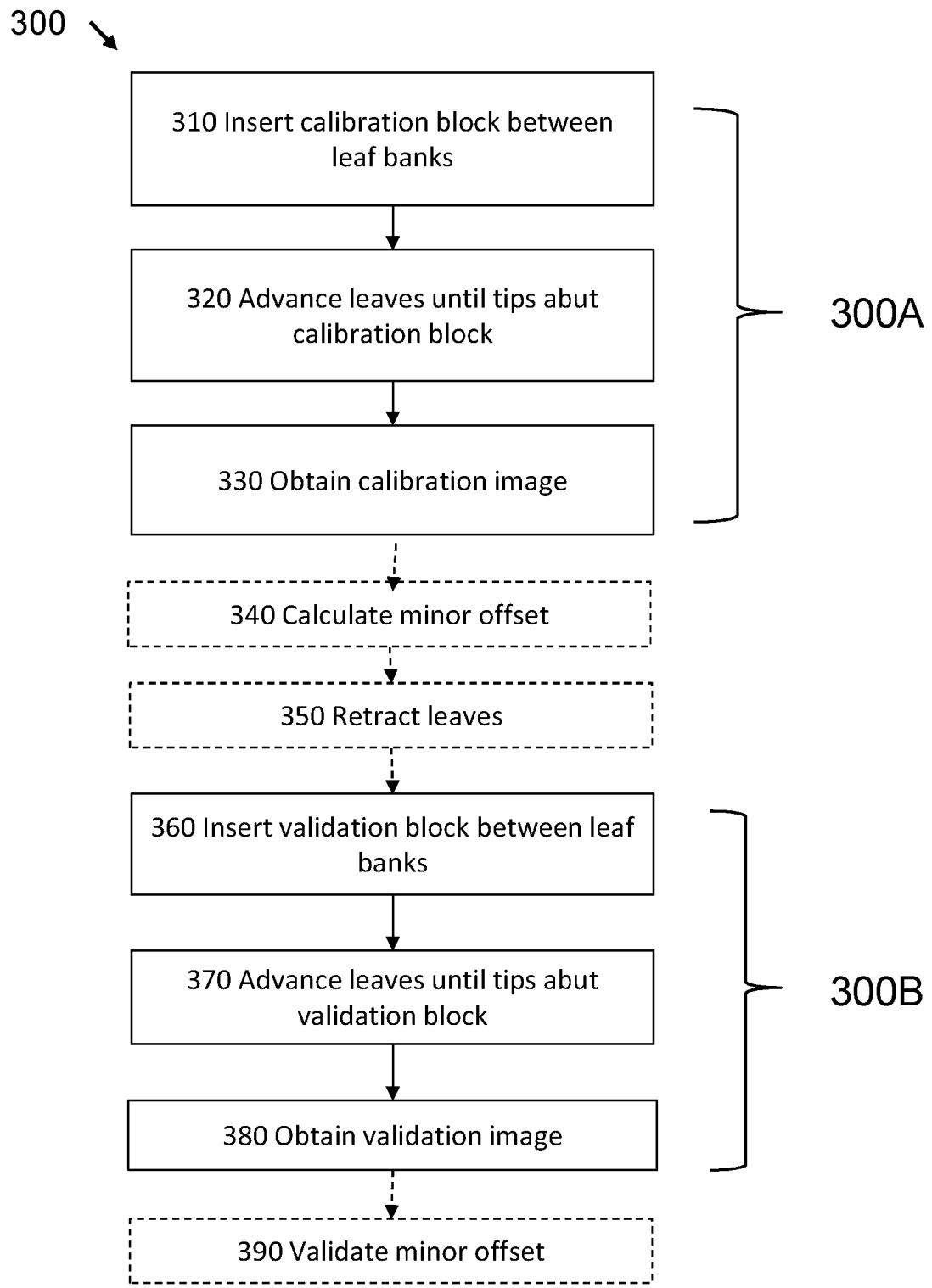
FIG. 3 is a flow diagram of a leaf imaging method, in accordance with an aspect of the present disclosure.

FIG. 3 illustrates an exemplary calibration method 300 for a multi-leaf collimator (e.g. MLC 200) in which minor offsets are quantified and used to determine the position of the leaf tips based on the detected positions of the collimator leaf markers.

300A is a method for obtaining a calibration image from which minor offset values of the leaves can be calculated. 300B is a method for obtaining a validation image from which the minor offset values can be validated.

Figure 8:
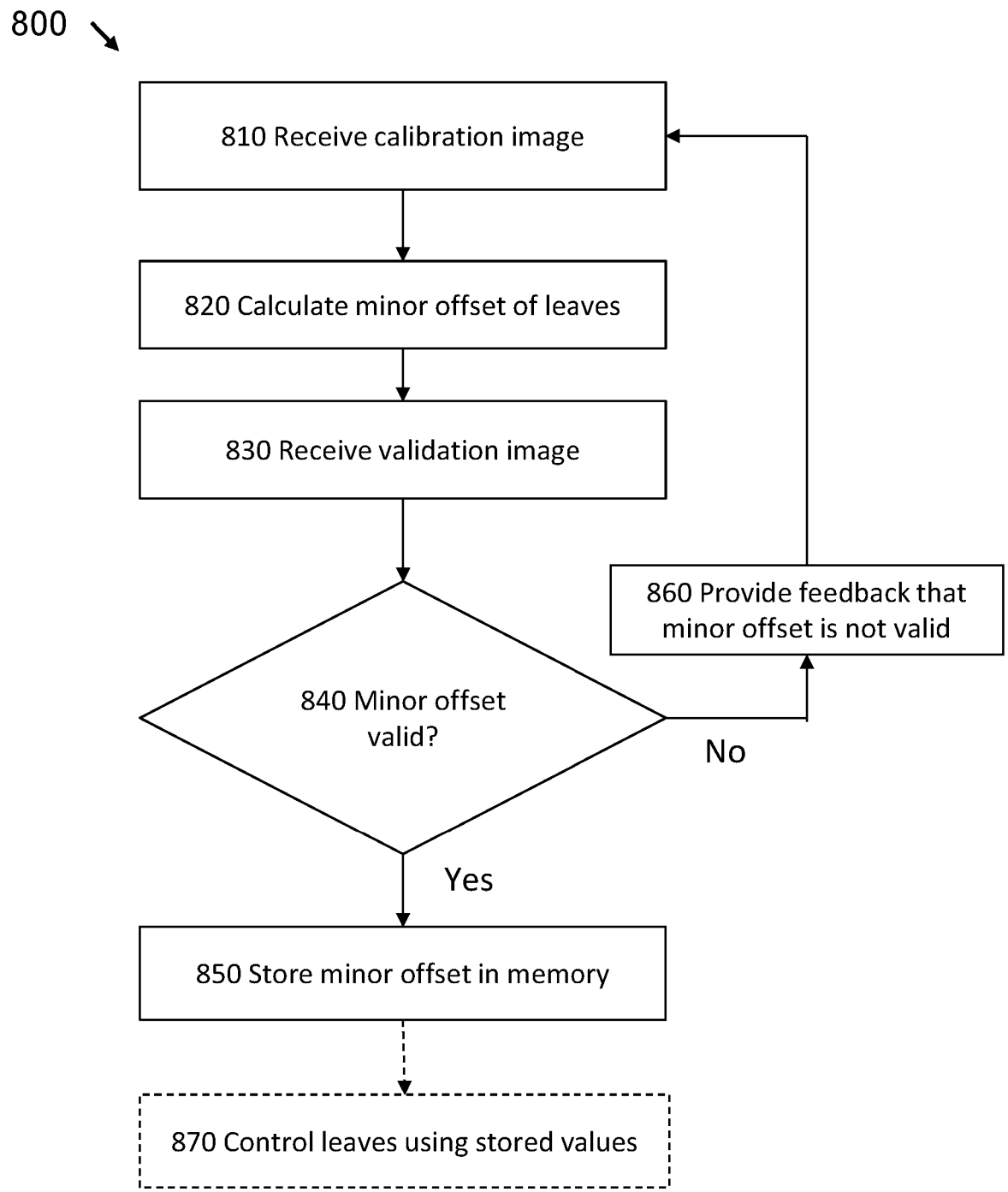
FIG. 8 is a computer implemented method of calibrating a multi-leaf collimator.

The steps in dashed lines are performed by a computer program on a processor, for example a computer program on a processor in controller 140. The method performed by the computer program is shown in more detail in FIG. 8. The steps in dashed lines need not be performed in the order shown in FIG. 3. For example, the processing of the images could take place after both of the images (the calibration image and the validation image) have been obtained.

Obtaining Calibration Image 300A is a method of obtaining a calibration image of multi-leaf collimator leaves. The calibration image can be used to calculate a value of the minor offset of the leaves. That is, the calibration image can be used to determine the distance between the leaf marker 242 and the leaf tip 206 for each leaf of the MLC 200.

Figure 4A:
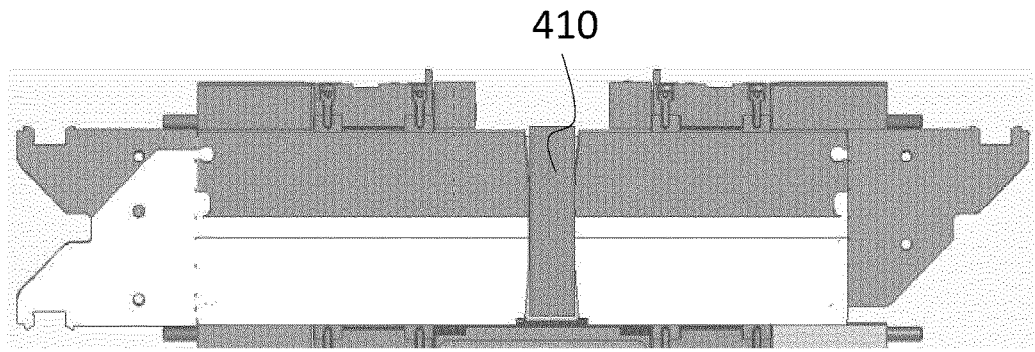
FIG. 4A is cross sectional view of two leaf banks in the calibration position.

At step 310 a calibration block is inserted between the two banks of leaves. One embodiment of a calibration block 410 is shown in FIG. 4A. The calibration block is mounted between the first and second banks of leaves. A technician or a controller inserts a calibration block 410 between the first bank of leaves (e.g. leaf bank 210) and the second bank of leaves (e.g. leaf bank 220).

The calibration block is inserted between the first and second banks of leaves (210 and 220). In the embodiment of FIG. 4 the calibration block 410 is elongate and is mounted such that the longitudinal centreline of the calibration block 410 lies parallel the centreline of the MLC.

To mount the calibration block in a fixed position a number of techniques can be used. Mounting blocks may be used. Alternatively collimation diaphragm leaves can be used to mount the calibration block.

The collimation diaphragm consists of two attenuation leaves movable perpendicular to the MLC leaves, which form the upper and lower delineation edges of the beam. The diaphragm leaves can be used to hold the calibration block in the intended orientation. The calibration block is inserted between the banks of leaves of the MLC. The diaphragm leaves are extended inwards perpendicular to the direction of travel of the MLC leaves to abut the ends of the calibration block and hold it at the correct orientation.

Alternatively, the outer leaves of the MLC could be fully extended over the ends of the calibration block and hold the block therebetween.

The calibration block 410 is made from a rigid material. In the embodiment of FIG. 4 the calibration block has a uniform thickness. In the present aspect the calibration block has a thickness of approximately 10 mm. In other aspects, the calibration block has a thickness, for example, between 9 mm and 11 mm, or between 8 mm and 12 mm.

At step 320, controller 140 advances the leaves of the first and second leaf banks towards the centreline. Controller 140 moves the leaves, including advancing and retracting the leaves, by actuation of leaf motors. The controller 140 moves the leaves until the tips of the leaves abut the calibration block. That is, the leaves of both banks are advanced until the tips of the leaves come into contact with the calibration block 410.

The calibration block is rigid, meaning that it does not deform upon contact with the leaves of the MLC. Therefore the tips of the leaves are aligned in a line along the edge of the calibration block. In the embodiment of FIG. 4 the calibration block 410 has a uniform thickness (thickness in the direction parallel to the direction of movement of the leaves), and the longitudinal axis lies parallel to the centreline of the MLC, therefore the tips of the leaves in each bank are aligned in a straight line parallel to the centreline of the MLC.

The leaves of the MLC are in the calibration position when the tips of the leaves each abut the calibration block 410.

At step 330, an image of the MLC in the calibration position is taken. The camera is used to image the MLC. The image of the MLC in the calibration position is known herein as the calibration image. The calibration image is sent to a processor, such as a processor of the controller 140.

Figure 4B:
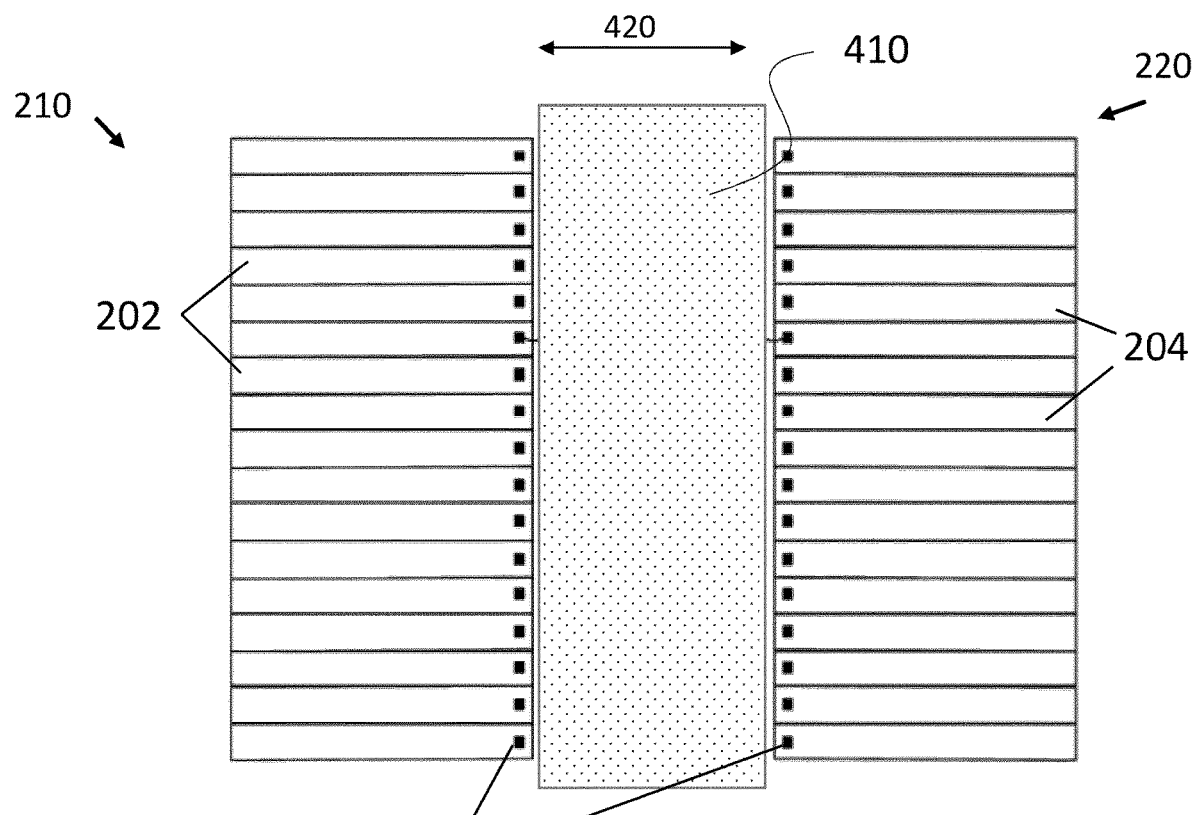
FIG. 4B is a top plan view of two leaf banks in the calibration position.

FIG. 4B shows a top view of the MLC in the calibration position. The leaves in both banks of leaves abut the calibration block 410, meaning that in each leaf pair the tips of the leaves are separated by a distance equal to the thickness of the calibration block 410.

The leaf markers 242 are visible in the calibration image. Since the markers on each leaf are positioned roughly the same distance from the leaf tip, the markers 242 of each leaf bank in the calibration position are also positioned approximately in a line equivalent to the edge of the calibration block. In the embodiment in FIG. 4, the edge of the calibration block is a straight line and therefore the markers in the calibration image are in approximately a straight line. The calibration block 410 is not visible in the image. Further, the leaves 204 are not visible in the image.

Since the markers 242 are visible by the camera and are visible in the calibration image, the two approximately straight lines of the markers are visible in the calibration image, despite the fact that the leaves of the MLC are not visible.

At step 340, the calibration image is processed by the processor 140 and used to calculate a value of the minor offset. Details of processing the calibration image to calculate the minor offset are given in FIG. 5. The minor offset is an offset of the marker relative to a reference location. The reference location is the tip of the leaf if calculating the absolute minor offset, or a reference marker of a leaf in the leaf bank if calculating the relative minor offset. This is discussed more below.

The minor offset may be calculated as the distance to the centre of mass of each marker.

Calculating the Minor Offset

Figure 5:
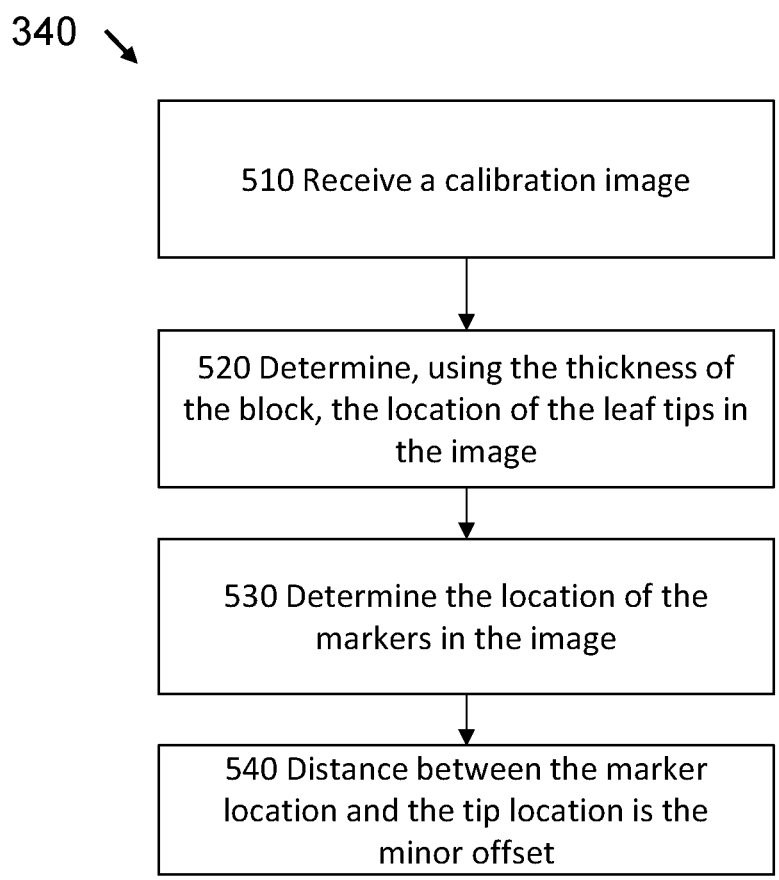
FIG. 5 is a is a flow diagram of a method of calculating the minor offset.

FIG. 5 illustrates a computer-implemented method, carried out at a processor of calculating a minor offset value for each leaf in a calibration image such as that obtained in 300A.

Some embodiments of the method disclosed herein can be used to calculate a relative minor offset, which is discussed below in the section entitled "relative minor offset". Other embodiments, such as the embodiment illustrated in FIG. 5, calculate an absolute minor offset for each leaf.

At step 510, the processor receives the calibration image from the camera. At step 520, the processor identifies the location of the edge of the calibration block in the image. Since, in the calibration position, the tips of the leaves abut the calibration block 410, the location of the edge of the calibration block 410 in the calibration image corresponds to the location of the tips of the leaves in the calibration image.

There are a number of ways the location of the edge of the calibration block is identified. In the implementation in which the block has a uniform thickness and is mounted with the longitudinal axis on the centreline of the MLC, the following method may be used to identify the edges of the calibration block in the image.

The processor first identifies the centreline of the MLC. As explained above, the camera is centred on the centreline of the MLC and therefore the image is centred on the centreline of the MLC. Since the calibration block 410 is centred on the centreline, the thickness of the calibration block can be used to identify the location of each edge of the calibration block in the image.

That is, half of the thickness 420 of the calibration block 410 lies on either side of the centreline 230. If the centre of the image is taken as x=0, the location of the edges of the calibration block lie at the lines $$x = +\frac{\text{thickness } 420}{2} \text{ and } x = -\frac{\text{thickness } 420}{2}.$$

This line is also the lateral location of the tips of the MLC leaves.

In other implementations, the edge of the block may be identified using different techniques.

In one implementation the block is inserted with the longitudinal axis aligned with an alignment line which is offset from the centreline by a known distance. Since the image is centred on the centreline, the alignment line can be located in the image using the known distance. Once the alignment line is located in the image, the thickness of the block is used to determine the location of the edges of the block using a similar method to that described above in step 520.

In other implementations, the calibration block is inserted with the edges at a known, predetermined location. The predetermined location is known and therefore can be identified in the image.

In implementations which the block does not have a uniform thickness (which are detailed below in the "non-uniform thickness" section) the thickness of the block and the known profile of the edges can be used to identify the edges of the block in the image relative to an alignment line.

In some implementations the block may be placed into a pre-determined outline by the technician. The location of this outline is known and identified in the image.

Alignment marks may be marked on the MLC to assist the technician in inserting the calibration block to the correct location.

At step 530, the processor 140 obtains the imaging marker position. That is, the processor determines, for each leaf, the location of the leaf marker 242 in the calibration image. The obtained imaging marker positions include the imaging marker position coordinates for the imaging marker of each leaf.

At step 540, the processor calculates the minor offsets 244 for each leaf in the bank. The minor offset is the lateral difference between the identified marker position in the image and a reference location. In the implementation in FIG. 5 the minor offset is the absolute minor offset, the distance between the located leaf tip (coincides with the located edge of the calibration block) and the identified marker position in the image. In other implementations the minor offset is the relative minor offset, as explained later in the description.

The processor calculates leaf position coordinates corresponding to the position of tips 206 of the collimator leaves which may include an x-coordinate and a y-coordinate of each leaf tip 206. For a given leaf at a given, the value of the minor offset may be subtracted from the value of the imaging marker x-coordinate to determine the value of the leaf position x-coordinate. In this way, the minor offset may be corrected for and the x-coordinate of the leaf tip identified. For a given leaf at a given position, the value of the leaf position y-coordinate may be equal to the value of the imaging marker y-coordinate. Because minor offset only distorts calculation of the leaf position along the x-axis, the y-coordinates of the leaves do not require correction for the minor offset.

At step 350 the leaves of the MLC are retracted away from the centreline so that the leaf tips no longer abut the calibration block. Once the leaves have been withdrawn, the calibration block 410 can be removed from the MLC. The calibration block can be removed by hand by the technician, or there could be an actuator in the radiotherapy device to insert and remove the blocks.

Obtaining Validation Image 300B is a method of obtaining a validation image of multi-leaf collimator leaves. The validation image can be used to validate the value of the minor offset of the leaves which has been calculated by the processor in step 340. Validation of the minor offset values is confirmation that each of the values of minor offset is accurate enough to fall within the thresholds of the device.

Optionally the validation image can also be used to validate the lens distortion. As explained above, the lens of the camera can distort the images of the markers. The extent of this distortion is different for each lens and can change every time adjustments are made to the camera; thus, a distortion correction technique developed for one camera may not be applicable to other cameras, or to the camera in question after servicing. The amount of distortion varies across the lens and therefore varies throughout the image. The lens distortion is calculated using other, known techniques, and stored in the processor.

Figure 6A:
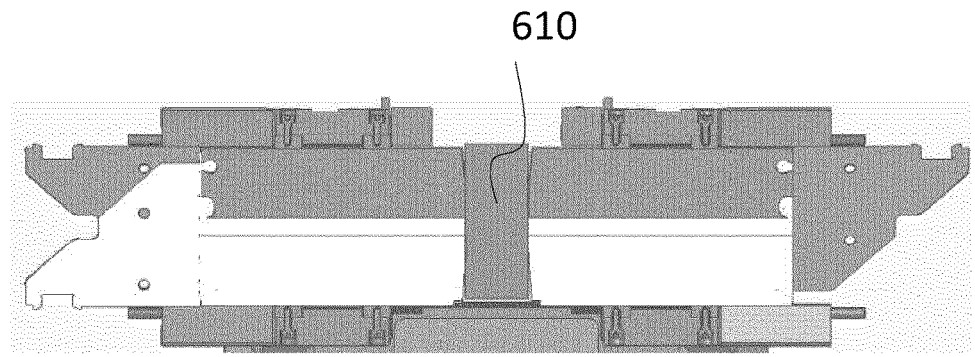
FIG. 6A is cross sectional view of two leaf banks in the validation position.

At step 360 a validation block is inserted between the two banks of leaves. The validation block 610 is shown in FIG. 6A. The validation block is mounted between the first and second banks of leaves in a similar way to the mounting of the calibration block. That is, a technician or controller inserts a validation block 610 between the first bank of leaves (e.g. leaf bank 210) and the second bank of leaves (e.g. leaf bank 220).

In the embodiment in FIG. 6 the validation block 610 is elongate and is mounted such that the longitudinal centreline of the validation block 610 lies parallel the centreline of the MLC.

The validation block 610 can be mounted as discussed above in relation to mounting of the calibration block. That is, the diaphragm leaves, or the outermost leaves of the MLC can be used to mount the validation block and hold it in a known orientation.

Like the calibration block 410, the validation block 610 is made from a rigid material. The validation block also has a known thickness. The validation block 610 has a different thickness 620 to the thickness of the calibration block 420.

In some embodiments the thickness of the validation block 610 is greater than the thickness of the calibration block 410. This provides the advantage of allowing for more accurate minor offset values to be calculated as is explained below.

In the embodiment of FIG. 6 the the validation block has a constant thickness of approximately 50 mm. In other aspects, the calibration block has a thickness, for example, between 9 mm and 11 mm, or between 8 mm and 12 mm.

At step 370, controller 140 advances the leaves of the first and second leaf banks towards the centreline. The controller 140 moves the leaves until the tips of the leaves abut the validation block 610. That is, the leaves of both banks are advanced until the tips of the leaves come into contact with the validation block 610.

The validation block is rigid, meaning that it does not deform upon contact with the leaves of the MLC. The MLC is in the validation position when the tips of the leaves each abut the validation block 610. In the embodiment of FIG. 6 the validation block 610 has a uniform thickness (thickness in the direction parallel to the direction of movement of the leaves), and the longitudinal axis lies parallel to the centreline of the MLC, therefore the tips of the leaves in each bank are aligned in a straight line parallel to the centreline of the MLC.

At step 380, an image of the MLC in the validation position is taken. The camera is used to image the MLC. The image of the MLC in the validation position is known herein as the validation image. The validation image is sent to a processor, such as a processor of the controller 140.

Figure 6B:
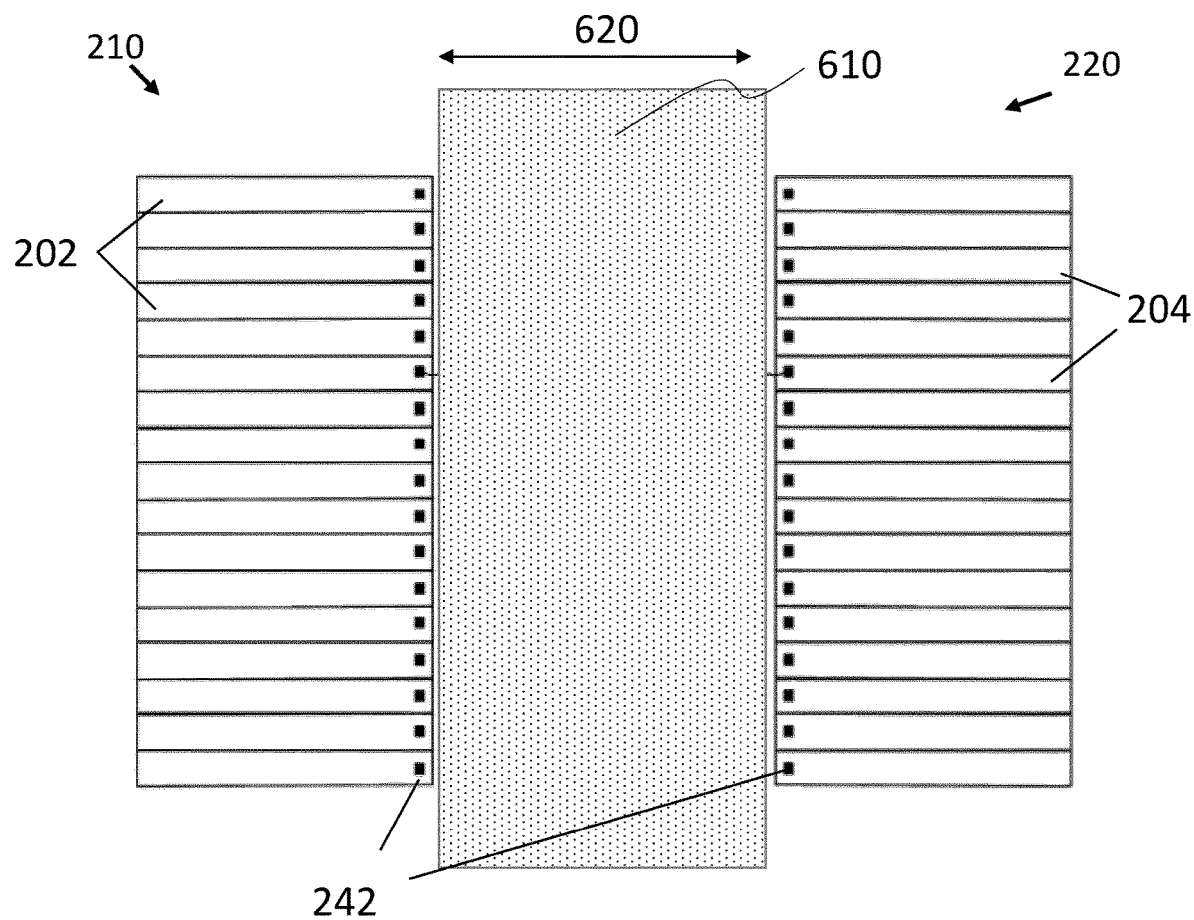
FIG. 6B is a top plan view of two leaf banks in the validation position.

FIG. 6B shows a top view of the MLC in the validation position. The leaves in both banks of leaves abut the validation block, meaning that in each leaf pair the tips of the leaves are separated by a distance equal to the thickness of the validation block 610.

The leaf markers 242 are visible in the validation image. Since the markers on each leaf are positioned roughly the same distance from the leaf tip, in an embodiment where the validation block has a uniform thickness the markers 242 of each leaf bank in the validation position are also positioned approximately in a straight line. The validation block 610 is not visible in the image. Further, the leaves 204 are not visible in the image.

Since the markers 242 are visible by the camera and are visible in the validation image, the two approximately straight lines of the markers are visible in the validation image, despite the fact that the leaves of the MLC are not visible.

At step 390, the validation image is processed by the processor 140 and used to validate the value of the minor offset as calculated in step 340. Details of processing the validation image to validate the minor offset are given below in FIG. 7.

In the above description separate calibration and validation blocks are described. In another implementation a single tool can be used as both a calibration block and a validation block. When inserted at a first orientation (for example, at step 310) the block acts as a calibration block and proves a first profile for the leaves to abut in the calibration position. The tool is then removed and rotated. It is reinserted at a second orientation (for example at step 360) to act as a validation block. At the second orientation the block provides a second profile for the leaves to abut in the calibration position. In this way a single tool is provided to perform the function of both the calibration block and the validation block.

Validating the Minor Offset

Figure 7:
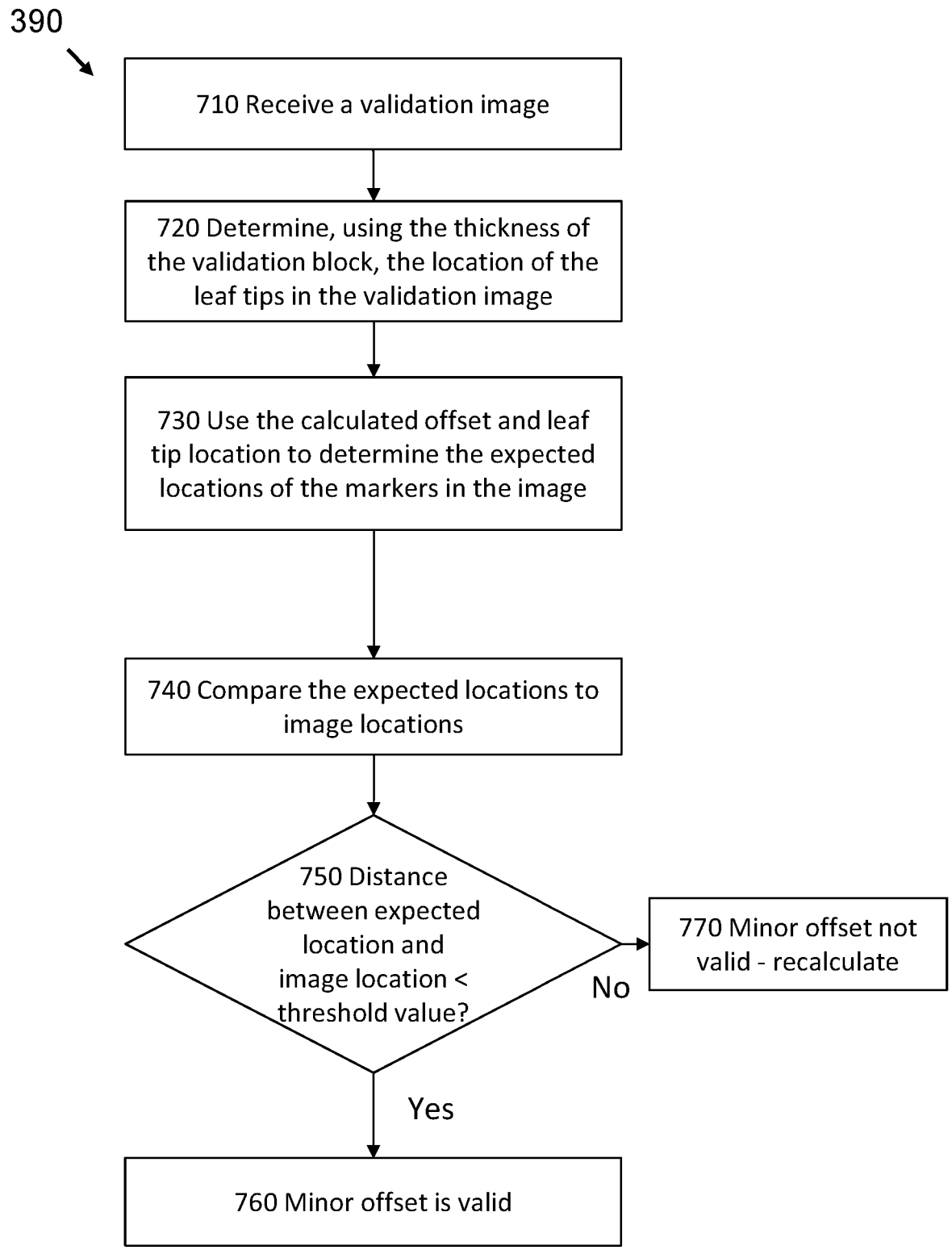
FIG. 7 is a flow diagram of method of validating the minor offset.

FIG. 7 illustrates a computer-implemented method, carried out at a processor of validating a minor offset value for each leaf in a validation image such as that obtained in 300B.

At step 710, the processor receives the validation image from the camera. At step 720, the processor identifies the location of the edge of the validation block in the image. In the validation position, the tips of the leaves abut the validation block 610, the location of the edge of the validation block 610 in the calibration image corresponds to the location of the tips of the leaves in the validation image.

The edges of the validation block can be identified using any technique such as those described above in relation to identifying the edges of the calibration block in step 520.

In the implementation in which the block has a known uniform thickness and is centred on the centreline of the MLC, the following steps may be used.

Half of the thickness 620 of the validation block 610 lies on either side of the centreline 230. If the centre of the image is taken as x=0, the location of the edges of the validation block lie at the lines $$x = +\frac{\text{thickness } 620}{2} \text{ and } x = -\frac{\text{thickness } 620}{2}.$$

This line is also the lateral location of the tips of the MLC leaves. As described above in relation to step 520, other methods may be used.

In one implementation the validation block is inserted with the longitudinal axis aligned with an alignment line which is offset from the centreline by a known distance. Since the image is centred on the centreline, the alignment line can be located in the image using the known distance. Once the alignment line is located in the image, the thickness of the validation block is used to determine the location of the edges of the block using a similar method to that described above in step 720.

In other implementations, the validation block is inserted with the edges at a known, predetermined location. The predetermined location is known and therefore can be identified in the image.

In implementations which the validation block does not have a uniform thickness (which are detailed below in the "non-uniform thickness" section) the thickness of the block and the known profile of the edges can be used to identify the edges of the block in the image relative to an alignment line.

In some implementations the block may be placed into a pre-determined outline by the technician. The location of this outline is known and identified in the image.

Alignment marks may be marked on the MLC to assist the technician in inserting the validation block to the correct location.

At step 730, the processor 140 calculates an expected location of each marker in the validation image. The expected location is the location the marker would be if the calculated distortion and minor offsets were correct.

The expected location is calculated by, for each leaf, calculating the total displacement of the marker by adding the calculated minor offset to the calculated edge of the validation block in the image.

The distortion value is also taken into account. The distortion is calculated using a known technique, and the calculated distortion is used to determine where the marker is expected to be in the image if both the minor offset and the calculated distortion are correct.

At step 740, for each leaf the actual location of the marker in the image is located and compared to the expected location of the marker. If the actual location of the marker and the expected location coincide, the distance between the two is zero and the image confirms the calculated minor offset and the calculated distortion.

If the actual location of the marker and the expected location of the marker do not coincide, the processor determines the distance between the actual location and the expected location.

At step 750 the distance between the actual location of the marker in the image and the expected location of the marker is compared to a threshold value. The threshold value is predetermined and stored in a memory associated with the processor. The threshold value may be input by a technician or may be determined at manufacture. If the distance is less than the threshold, then the calculated minor offset value and the distortion are determined to be acceptable and within the tolerance of the machine. The minor offset and the distortion are determined to be valid (step 70).

If the distance between the location of the marker in the image and the expected location of the marker is greater than the threshold, then then calculated minor offset and the distortion are not within the acceptable tolerance. The minor offset and the distortion are determined not to be valid (step 770).

Steps 720 to 760/770 are performed for each leaf, using the calculated minor offset of the respective leaf and the image location of the leaf marker of that leaf. It may be that the calculated minor offset or some of the leaves of the MLC are determined to be valid, whereas the calculated minor offset for the remining leaves of the MLC are determined to not be valid.

Once validated, the value of the minor offset for each leaf is output. The value may be saved to the memory 142 of the device. The minor offset of each leaf is stored in the memory and can be used in future radiotherapy procedures. That is, once the minor offset is calculated and saved, the MLC need not be calibrated before every use of the radiotherapy device. Once the MLC has been calibrated through calculation of the minor offsets, these values can be saved in the device and used in future use of the MLC.

The minor offsets are used in radiotherapy to accurately calculate the position of the tip of the leaf of the multi-leaf collimator. The minor offsets are used to determine the position of the leaf tips based on the detected positions of the collimator leaf markers. The position of the tips of the leaves must be known during treatment so that the shape of the beam of radiation, and therefore the dose of radiation being delivered to a patient, is known.

During treatment the leaves are controlled by the controller to create a desired beam shape. The leaves are imaged by the camera so that the position of the leaves can be checked against the treatment plan i.e. to ensure that the leaves are in the expected position and the beam is delineated according to the treatment plan. The leaves themselves may not be visible in the image. In some examples the leaves may be partially visible. Leaf markers 242 are visible in the image. For each leaf, the location of the leaf marker 242 in the image is used with the corresponding minor offset for that leaf to calculate the absolute position of the leaf tip.

Once the absolute position of the leaf tip is known, this is used to determine the collimation being provided by the leaf during treatment. The MLC is controlled based on the calculated position of the leaf tip using the minor offset. For example, if it is determined from the image of the MLC during treatment that the leaf tip needs to be extended or withdrawn from the beam to align with the treatment plan, the controller controls the leaf as necessary.

The blocks may be inserted by hand by a technician or operator. There may be markings on the MLC such that the operator can align the centre of the calibration/validation block with the centreline of the MLC.

Alternatively the blocks could be in included in an adaptor which fits onto an accessory ring for the MLC. The blocks may be moved into position by an actuating means the device rather than by hand. As explained below, the actuating means may comprise a diaphragm in the radiation head.

Computer-Implemented Method

Method 800 is a processor-executed method. In some embodiments, the steps of method 800 are executed by a same processor in the radiotherapy device, such as a processor in controller 140. Alternatively, one or more steps of method 600 can be executed by separate processors.

Alternatively, the method may be performed at a location remote from the radiotherapy device, such as at a central server where the images are received over a network.

At step 810, the processor receives a calibration image of the MLC from the camera. The calibration image may have been obtained using the steps in 300A. The calibration image may have been obtained at any time. For example, the method 800 may begin as soon as a technician has obtained a calibration image. Alternatively, the calibration image may have been obtained an amount of time ago.

At 820 the processor calculates the minor offset of each leaf. This may be done using the location of the markers 242 in the image and the known profile of the calibration block. The minor offset can be calculated using the method in FIG. 5. The minor offsets may be stored in a memory.

At step 830 the processor receives a validation image of the MLC from the camera. The validation image may have been obtained using the steps in 300B. The validation image may have been obtained at any time. For example, the validation image may have been obtained before the calibration image.

At 840 the processor determines, from the validation image, whether the minor offset calculated in step 820 is valid. This is done by comparing an expected location of a marker in the image, which is calculated using the profile of the validation block and the calculated minor offset, to the location of the marker image. If the difference between the two is below a threshold value, the calculated minor offset is valid. The expected location can be calculated using the method in FIG. 7.

If the calculated minor offset is determined to be valid, the minor offset is outputted, for example sent to a processor of the radiotherapy device or stored in a memory at step 850. The memory may be a memory located at the radiotherapy device, such as memory 142, or may be stored at a remote location. The calculated minor offsets of each leaf of the plurality of leaves are outputted as calibration values.

In step 870 the calibration values are used to control the leaves of the MLC. This step is optional and is not essential in the method of calibrating the MLC.

If, at step 840 the minor offset is determined not to be valid, the processor provides feedback that the minor offset is determined not to be valid. This feedback may be a message to an operator via a user interface. Alternatively, the feedback may be a message to prompt re-analysis of the calibration image to re-calculate the minor offset of the leaves.

Step 840 may also comprise including a lens distortion value in calculating an expected location of the markers in the image. The lens distortion value is calculated using other, known techniques, and stored in the processor. If the locations of the markers in the validation image are within a threshold value of the expected location, both the minor offset and the lens distortion are determined to be valid. If the locations of the markers in the validation image are not within a threshold value of the expected location, either the calculated minor offsets, or the lens distortion value, or both, are not valid.

Non-Uniform Thickness

In the embodiments in FIGS. 4 and 6 the calibration block and the validation block each have a uniform thickness. When the calibration/validation blocks have a uniform thickness, in the calibration/validation positions the tips of the leaves are aligned in a straight line. In this way the relative offset of the leaf markers is known. That is, the position of each of the leaf markers relative to the other markers in order to have the leaves in a straight line is known. In this way, during treatment the relative offsets of the markers in the image can be used to determine the relative offset of the tips of the leaves. Accordingly, the shape formed by the edge of the bank of leaves is known.

It will be apparent that to the minor offset can be calculated using a calibration block of any known thickness. That is, the calibration block need not be of a uniform thickness.

Figure 9:
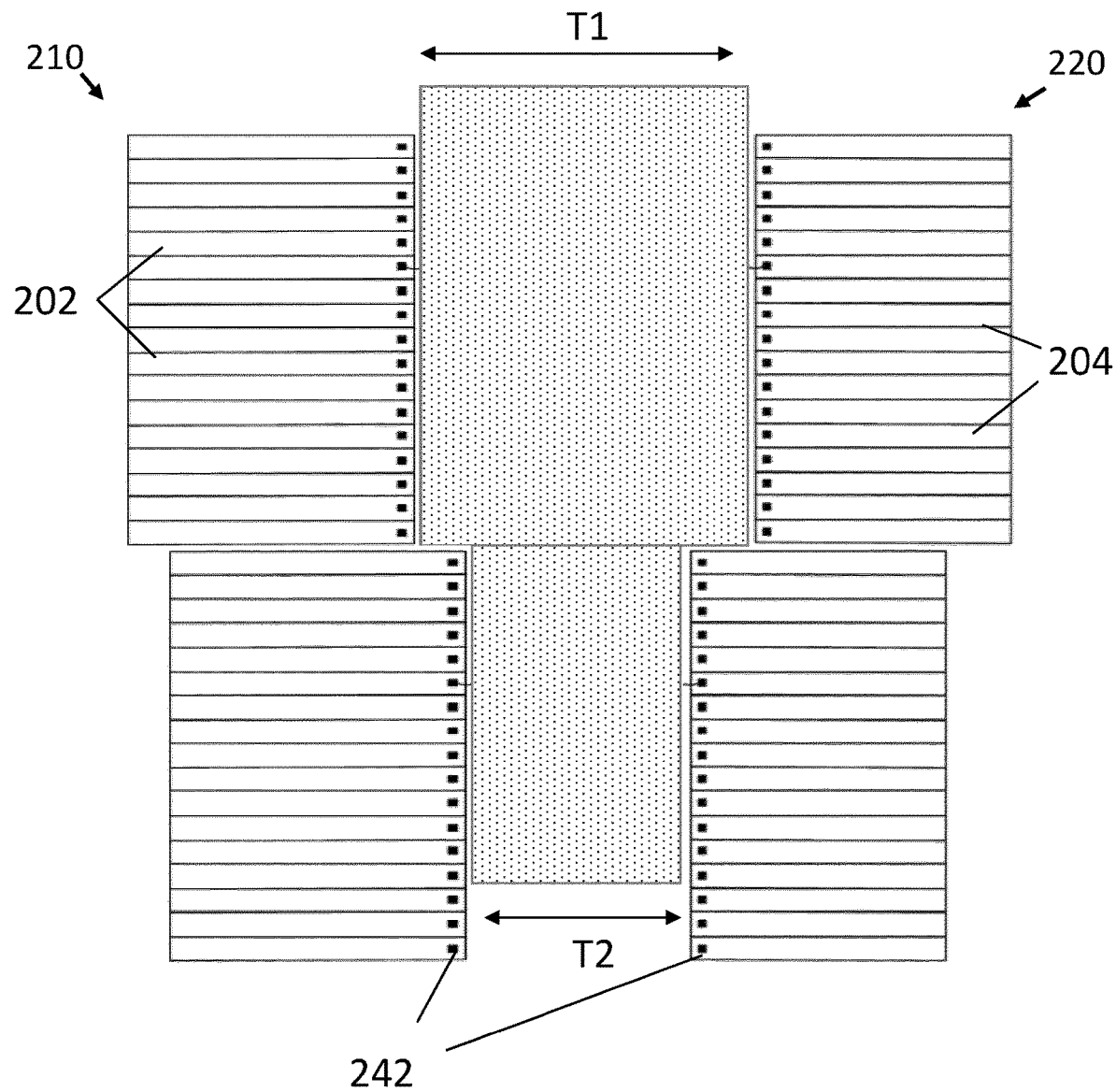
FIG. 9 is a top plan view of two leaf banks in a calibration position.

For example, a calibration block having a stepped thickness such as that shown in FIG. 9 could be used. The calibration block has a first thickness T1 and a second thickness T2. When the leaves are in the calibration position, the shape being formed by the edge of the leaf bank is known. This shape is the shape of the edge of the block. Instead of a straight line, as in the example in FIG. 4, the leaf tips in one bank form a stepped edge.

In the same way as the above examples, the locations of the leaf markers 242 in the calibration image can be used to obtain values for the minor offsets of the markers.

The same is true of the validation block—any shape can be used in which the relative position of the leaf tips is known. This allows for the calculation of the minor offset of the leaf markers.

The 'profile' of the edges of the calibration/validation blocks is referred to herein. The profile is the shape of the edge of the block which the leaf tips abut. The profile of each of the edges of a block having uniform thickness, for example the calibration black in FIG. 4 or the validation block in FIG. 6 is a straight line. The profile of each edge of the calibration block illustrated in FIG. 9 is a stepped shape.

Figure 10A:
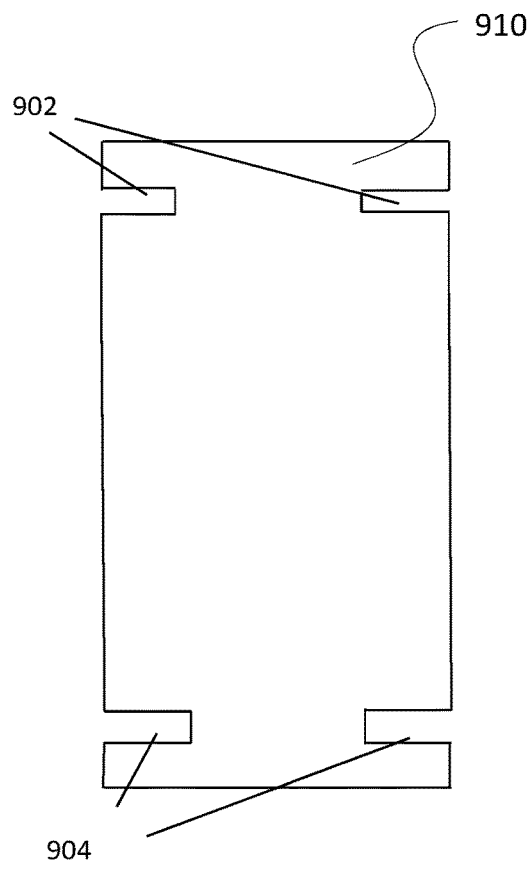
FIGS. 10a and 10b show calibration blocks having castellations.

In some implementations the calibration block and/or the validation block may have castellations. A castellation is a recess in the profile of the block, shaped to accommodate one or more MLC leaves which abut the inner edge of the protrusion. Alternatively, a castellation may be a protrusion from the edge of the block, shaped such that one or more MLC leaves abut the protrusion. FIG. 10*a* shows a block 910 having a pair of opposing castellations 902, 904 at each end of the block. The 'block' 910 can either be a calibration block or a validation block. In use, when the leaves are positioned to abut the edges of the block, end leaf of each leaf bank fits into a castellation and abuts the edge of the castellation. In this way the block is able to correctly self-locate between the leaf banks. The castellation is shaped such that it houses the leaf, and negligible longitudinal movement is possible such that the castellations ensure that the longitudinal positioning of the calibration block in the field is correct.

As will be appreciated, other arrangements of castellations on the calibration (or validation) blocks may be included. In another implementation the edge of the block is shaped such that each leaf pair abuts a different castellation along at least a portion of the edge of the block. The block shown in FIG. 10*b* has a plurality of castellation 'steps', 906 and 908. A leaf abuts each castellation, or step, creating a pattern which follows the shape of the castellations on the block. The block can be shaped such that the distance between the leaves abutting each either side of the block varies to cover the full field, or a larger portion of the full field. This use useful to map non-linearity across the optics.

Figure 10B:
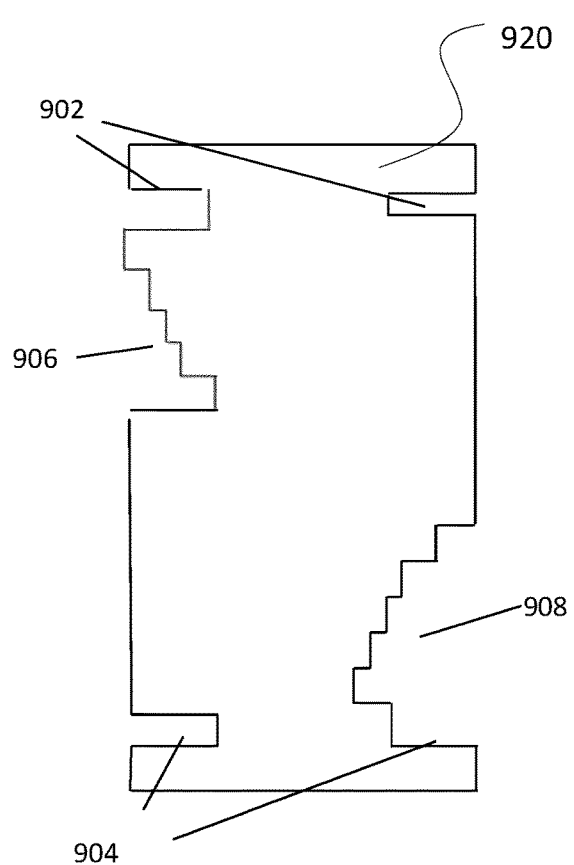

In some examples the castellations are asymmetrical to provide a different profile depending on the orientation of the block. In FIG. 10*b* it can be seen that the castellation pattern 906 on the top left of the block is different to the castellation pattern 908 on the bottom right of the block. That is, the profile of the block is asymmetric on 180 degree in-plane rotation. The block 910 can therefore be inserted at different orientations to provide different profiles, with the profile provided at a first orientation being different to the profile provided at a second orientation. Using the block at two different orientations increases the field which is covered by the leaves in the calibration or validation position. This is useful to map the non-linearity of the optics using a single block. The different orientation could be provided by rotating around one or more of three axes (i.e. rotation in plane, flipping 'horizontally', flipping 'vertically'). In some examples a block may have castellations on all four sides, and be asymmetric such that each 90 degree rotation in-plane provides a different profile.

Using a block with stepped castellations and/or asymmetric castellations provides a single tool which can be used such that, in the calibration and/or validation position the distance between the leaves covers a large portion of the field, or covers the full field. Alternatively, multiple tools can be used, each block having a different profile, to cover the full range of the field.

In other implementations a block with symmetrical castellations is provided. In FIG. 10b the castellations are adjoined continuous steps, with adjacent leaves abutting adjacent steps. In other examples the block may include separated individual castellations of different depths each having a width to accommodate a single leaf or multiple leaves.

Hence there is also provided a block for calibration and/or validation of leaf marker offset. The block may be used in the methods disclosed herein. In implementations at least one side of the block has a profile comprising at least one castellation. The slide of the block may comprise a profile having a generally or substantially straight edge with at least one castellation. In this way, when leaves of a leaf bank abut the side, at least one leaf is extended to a greater or lesser extent than the other leaves. Optionally two opposing sides of the block each comprise a profile with at least one castellation. Each side may have a profile with a generally straight edge and at least one castellation.

Optionally the castellation is shaped to accommodate a single leaf from the leaf bank. The castellation is substantially the same width as a leaf. In use (when leaves are extended to abut the side of the block) the single leaf is extended to a greater extent than other leaves in the leaf bank. In this way the block can self-locate between two leaf banks when in use.

In some examples a castellation may accommodate more than one leaf of the MLC. For example, a castellation configured to accommodate two MLC leaves will have a width substantially the same as (although slightly larger than) the width of two MLC leaves.

Optionally two opposing sides of the block each comprise two castellations. Each castellation is sized to accommodate a single leaf from the leaf bank. The castellations are located to accommodate the end leaf of each leaf bank, such that in use the end leaf of each leaf bank is extended to a greater extent that the other leaves in the leaf bank. This provides improved ability of the block to self-locate between the leaf banks.

Optionally at least one side of the block comprises a profile having a plurality of castellations, each castellation being of a different depth. In this way, leaves abutting the castellation in use are extended to a different extent. The castellations may be sized to accommodate one leaf, or to accommodate a plurality of leaves. In some implementations the block comprises a plurality of stepped castellations. By providing castellations having different depths along the profile of the side of the block, in use the leaves are extended to a plurality of different degrees, allowing to map non-linearities in the optics.

Optionally, the castellations are asymmetrical, such that the profile of the block is asymmetrical under rotation. The block may be asymmetric under rotation around one or more of three axes: a first axis orthogonal to the plane of the block, and either of two axes mutually orthogonal to the first axis. Using an asymmetrical block at two different orientations increases the field which is covered by the leaves un use, which is useful to map the non-linearity of the optics using a single block.

In other implementations correctly locating the validation/calibration block could be achieved using diaphragms in the radiation head. The radiation head includes, for beam shaping purposes, diaphragms such as field-defining diaphragms positioned above or below the multi-leaf collimator. These diaphragms are controllable to extend into the beam to a greater or lesser extent. The diaphragms could be controlled to correctly locate the calibration or validation block, which may include positioning or squaring the block, between the leaf banks.

Relative Minor Offset

The embodiments in FIGS. 5 and 7 disclose calculating the absolute minor offset of the leaves of the MLC, and validating the minor offset. The absolute minor offset is the distance between the leaf tip and the leaf marker for any given leaf. To calculate the absolute minor offset, the location and profile of the edge of the calibration block in the calibration image must be known. In the embodiment in FIG. 5 this is determined using the thickness of the block.

As explained above, the absolute minor offset can be used to determine the location of the leaf tip of a given leaf based on an image of the marker and the calculated minor offset.

In some embodiments, a relative minor offset is calculated and/or validated. A relative minor offset is the minor offset (distance between the leaf marker and leaf tip) of a specific leaf relative to a reference minor offset (distance between the leaf marker and leaf tip) of a reference leaf in the leaf back of the MLC. The relative minor offset be used to determine the relative position of the tips of the leaves—i.e. the shape of the edge defined by the leaf tips—rather than the exact location of the tips of the leaves.

To calculate the relative minor offset, and therefore the shape defined by the leaves, the profile of the edge of the calibration block must be known. The exact location of the block, for example whether the block is centred on the centre line or positioned off-centre, does not need to be known to calculate the relative minor offset.

Advantages

Every feature of a leave used for calibration required machining to a very tight tolerance. Machining to tight tolerances is time consuming and expensive. Additionally, the more components or features which require machining to tight tolerances can introduce more inaccuracies into calibration measurements. Therefore, it is desirable to provide a method of determining the minor offset of the leaves which does not require any additional parts or dimensions which must be machined to tight tolerances.

This restricts the ultimately achievable calibration accuracy, increases cost, device complexity and reliability. Other errors and noise exist in known calibration techniques which affect calibration to a greater or lesser extent. For example, lens distortion affects different locations of the image by different amounts. It is beneficial to minimize the effect these have on leaf calibration. The current position sampling locations of the leaves effect the extent that the distortions have on leaf calibration.

The present method allows for the determination of the minor offset which does not rely on any additional components of the MLC being machined to tight tolerances. The MLC components used in the determination of the minor offset are the two components which are directly involved—that is the leaf marker and the leaf tip. Two blocks, each having a uniform known thickness are required. A uniform block which is not an integral component of the MLC is relatively simple to machine to an accurate and uniform thickness.

The solution provided is more simple and more accurate than including a feature which requires tight tolerance on each leaf of the MLC with which to calculate the minor offset.

Additionally, the calibration block is thinner than the validation block. The thickness of the calibration block is selected so that in the calibration position the leaf tips of the MLC lie close to the centreline. The distortion effect of the lens is minimal at the centre of the lens, being the centreline of the MLC. Therefore the image used to calculate the minor offset, the effects of distortion are minimised meaning the minor offset can be calculated more accurately.

In the validation image the leaf tips are further from the centreline meaning that distortion has a larger effect on the leaf tips and leaf markers in the validation image. This means that the combined effect of the calculated minor offset and the determined distortion can be validated using the validation image.

There is provided a method for calculating minor offset of leaves of an MLC and of validating the calculated minor offset.

In one aspect there is provided a method of calculating a minor offset as described above and illustrated in the figures, and in one aspect there is provided a method of validating a calculated minor offset as described above and illustrated in the figures. In one aspect there is provided a method of calculating a minor offset and validating the calculated minor offset.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A computer-implemented method for calibrating a multi-leaf collimator of a radiotherapy device, the multi-leaf collimator comprising a plurality of leaves, each leaf comprising an imaging marker, wherein the radiotherapy device includes an imaging device configured to image the plurality of leaves, the method comprising:
receiving, from the imaging device, an image of the multi-leaf collimator in a calibration position, wherein in the calibration position one or more tips of the plurality of leaves abut an edge of a rigid calibration block, the edge having a specified calibration profile;
calculating for each leaf of the plurality of leaves, from the calibration profile and a location of the imaging marker in the image, an offset of the imaging marker relative to a reference point; and
outputting one or more calibration values based on the calculated offsets, wherein at least one leaf of the multi-leaf collimator is controlled based on the one or more calibration values.

2. The method of claim 1, wherein in the calibration position, the rigid calibration block has a specified location.

3. The method of claim 2, wherein calculating the offset comprises calculating the offset of a center of mass of each imaging marker from a tip of a respective leaf of the plurality of leaves by:
identifying a location of the block in the image;
determining, using the calibration profile, the location of the edge of the block in the image; and
calculating the offset between the location of the imaging marker in the image and the location of the edge of the block.

4. The method of claim 3, further comprising:
receiving, from the imaging device, a validation image of the multi-leaf collimator in a validation position, wherein in the validation position the one or more tips of the plurality of leaves abut a rigid validation block having a specified validation profile and a specified location;
determining a location of the one or more tips of the plurality of leaves in the validation image;
calculating, from the location of the one or more tips of the plurality of leaves in the validation image and the calculated offsets for each leaf of the plurality of leaves, expected marker locations for each leaf imaging marker;
comparing the imaging marker locations in the validation image with the expected marker locations; and
determining, based on the comparison, whether the calculated offsets for each leaf of the plurality of leaves are valid.

5. The method of claim 4, wherein determining whether the calculated offsets are valid comprises:
comparing a distance between the calculated location and the imaging marker location in the validation image to a threshold; and
in response to the distance being below the threshold, determining that the calculated offsets for each leaf of the plurality of leaves are valid.

6. The method of claim 4, wherein the multi-leaf collimator includes two banks of opposing leaves opposed about a centerline; wherein in the calibration position, the rigid calibration block is centered on the centerline and wherein in the validation position the validation block is centered on the centerline.

7. The method of claim 4, wherein calculating an expected marker location includes applying a calculated lens distortion factor.

8. The method of claim 1, further comprising:
receiving, from the imaging device, a validation image of the multi-leaf collimator in a validation position, wherein in the validation position the one or more tips of the plurality leaves abut a rigid validation block having a specified validation profile;
determining, using the validation profile, a location of the one or more tips of the leaves in the validation position;
calculating, from the location of the one or more tips of the leaves in the validation position and the calculated offsets for each leaf of the plurality of leaves, expected marker locations for each leaf imaging marker;
comparing the imaging marker locations in the validation image with the expected marker locations; and
determining, based on the comparison, whether the calculated offsets for each leaf of the plurality of leaves are valid.

9. The method of claim 8, wherein the rigid calibration block has a uniform first thickness, and the validation block has a uniform second thickness, wherein the second thickness is greater than the first thickness.

10. The method of claim 8, wherein the rigid calibration block has a uniform have a thickness greater than or equal to 50 mm.

11. The method of claim 1, wherein the rigid calibration block has a uniform thickness of approximately 10 mm.

12. The method according to claim 1, wherein the reference location is an imaging marker of a selected leaf of the plurality of leaves.

13. A non-transitory computer-readable medium with instructions stored thereon that, when executed by a processor included on a radiotherapy device, cause the processor to:
receive, from an imaging device included on the radiotherapy device, an image of a multi- leaf collimator of the radiotherapy device in a calibration position, wherein the multi-leaf collimator includes a plurality of leaves, wherein each leaf of the plurality of leave comprises an imaging marker, and wherein in the calibration position one or more tips of the plurality of leaves abut an edge of a rigid calibration block, the edge having a specified calibration profile;
calculating for each leaf of the plurality of leaves, from the calibration profile and a location of the imaging marker in the image, an offset of the imaging marker relative to a reference point; and
outputting one or more calibration values based on the calculated offsets for each leaf of the plurality of leaves, wherein at least one leaf of the multi-leaf collimator is controlled based on the one or more calibration values.

14. The non-transitory computer-readable medium of claim 13, wherein in the calibration position, the rigid calibration block has a specified location.

15. The non-transitory computer-readable medium of claim 13, wherein calculating the offset comprises calculating the offset of a center of mass of each imaging marker from a tip of a respective leaf of the plurality of leaves including by:
identifying a location of the block in the image;
determining, using the calibration profile, the location of the edge of the block in the image; and
calculating the offset between the location of the imaging marker in the image and the location of the edge of the block.

16. The non-transitory computer-readable medium of claim 13, wherein the instructions further cause the processor to:
receive, from the imaging device, a validation image of the multi-leaf collimator in a validation position, wherein in the validation position the one or more tips of the plurality leaves abut a rigid validation block having a specified validation profile;
determine, using the validation profile, a location of the one or more tips of the leaves in the validation position;
calculate, from the location of the one or more tips of the leaves in the validation position and the calculated offsets for each leaf of the plurality of leaves, expected marker locations for each leaf imaging marker;
compare the imaging marker locations in the validation image with the expected marker locations; and
determine, based on the comparison, whether the calculated offsets for each leaf of the plurality of leaves are valid.

17. A radiotherapy device comprising:
a source of therapeutic radiation configured to produce a beam of therapeutic radiation;
a multi-leaf collimator configured to delimit the beam of radiation, the multi-leaf collimator comprising a plurality of individually movable leaves, each leaf comprising an imaging marker;
an imaging device configured to image the leaves; and
a non-transitory computer-readable medium with instructions stored thereon that, when executed by a processor of the radiotherapy device, cause the processor to:
receive from an imaging device included on the radiotherapy device, an image of a multi-leaf collimator of the radiotherapy device in a calibration position, wherein the multi-leaf collimator includes a plurality of leaves, wherein each leaf of the plurality of leaves comprises an imaging marker, and wherein in the calibration position one or more tips of the plurality of leaves abut an edge of a rigid calibration block, the edge having a specified calibration profile;
calculate for each leaf of the plurality of leaves, from the calibration profile and a location of the imaging marker in the image, an offset of the imaging marker relative to a reference point; and
output one or more calibration values based on the calculated offsets for each leaf of the plurality of leaves, wherein at least one leaf of the multi-leaf collimator is controlled based on the one or more calibration values.

18. The radiotherapy device of claim 17, further comprising a rigid calibration block having an edge with a specified calibration profile and a validation block having an edge with a specified validation profile.

19. The radiotherapy device of claim 18, wherein at least one of the calibration or validation block comprises a side having a profile comprising at least one castellation for accommodating one or more leaves of the plurality of leaves.

20. The radiotherapy device of claim 18, further comprising:
an actuator configured to selectively move the rigid calibration block and the validation block into an imaging position, wherein in the imaging position at least one of the calibration block or the validation block is located in a path of the plurality of leaves.

* * * * *